United States Patent
Wada et al.

(10) Patent No.: US 11,246,847 B2
(45) Date of Patent: Feb. 15, 2022

(54) ANTICANCER DRUG EFFECT ENHANCER

(71) Applicant: Delta-Fly Pharma, Inc., Tokushima (JP)

(72) Inventors: Hiromi Wada, Kyoto (JP); Tatsuhiro Ishida, Tokushima (JP); Kiyoshi Eshima, Tokushima (JP)

(73) Assignee: Delta-Fly Pharma, Inc., Tokushima (JP)

( * ) Notice: Subject to any disclaimer, the term of this patent is extended or adjusted under 35 U.S.C. 154(b) by 0 days.

(21) Appl. No.: 17/267,337

(22) PCT Filed: Feb. 5, 2020

(86) PCT No.: PCT/JP2020/004226
§ 371 (c)(1),
(2) Date: Feb. 9, 2021

(87) PCT Pub. No.: WO2021/009950
PCT Pub. Date: Jan. 21, 2021

(65) Prior Publication Data
US 2021/0228517 A1    Jul. 29, 2021

(30) Foreign Application Priority Data
Jul. 18, 2019 (JP) .............................. JP2019-132679

(51) Int. Cl.
*A61K 31/194* (2006.01)
*A61P 35/00* (2006.01)
*C07K 16/28* (2006.01)

(52) U.S. Cl.
CPC ............ *A61K 31/194* (2013.01); *A61P 35/00* (2018.01); *C07K 16/2818* (2013.01)

(58) Field of Classification Search
None
See application file for complete search history.

(56) References Cited

U.S. PATENT DOCUMENTS

2016/0304607 A1* 10/2016 Sadineni ............ C07K 16/2878
2020/0138855 A1   5/2020 Wada et al.
2020/0237906 A1*  7/2020 Li ........................... A61P 35/00
2020/0368273 A1  11/2020 Wada et al.

FOREIGN PATENT DOCUMENTS

JP         6359198 B1        6/2018
WO    WO-2018/028383 A1    2/2018
WO    WO-2019/016928 A1    1/2019
WO    WO-2019/142490 A1    7/2019

OTHER PUBLICATIONS

U.S. Appl. No. 16/962,990, filed Jul. 2020, Wada; Hiromi.*
Abe et al., "Caffeine citrate enhanced cisplatin antitumor effects in osteosarcoma and fibrosarcoma in vitro and in vivo," BMC Cancer, Jul. 15, 2019, 19(689): 1-11.
Azzarito et al., "Effect of Modified Alkaline Supplementation on Syngenic Melanoma Growth in CB57/BL Mice," PLOS One, Jul. 22, 2016, 11(7):e0159763, 1-13.
Cardone et al. "The Role of Disturbed Ph Dynamics and the NA /H Exchanger in Metastasis," Nature Reviews Cancer, Oct. 2005, 5:786-795.
Decision to Grant a Patent dated Nov. 10, 2020 in JP 2020-542334, with English translation.
Faes et al., "Acidic tumor microenvironment abrogates the efficacy of mTORC1 inhibitors," Molecular Cancer, 2016, 15:78(1-11).
Hamaguchi et al., "Effects of an Alkaline Diet on EGFR-TKI Therapy in EGFR Mutation-positive NSCLC," Anticancer Research, 2017, 37:5141-5145.
Harguindey et al., "The role of pH dynamics and the Na+/H+ antiporter in the etiopathogenesis and treatment of cancer: Two faces of the same coin—one single nature," Biochimica et Biophysica Acta, 2005, 1756:1-24.
Office Action and Search Report dated Feb. 24, 2021 in TW 109103632.
Office Action dated Sep. 8, 2020 in JP 2020-542334, with English translation.
Pilon-Thomas et al., "Neutralization of Tumor Acidity Improves Antitumor Responses to Immunotherapy," Cancer Research, Dec. 30, 2015, 76(6):1381-1390.
Ren et al., "Citrate Suppresses Tumor Growth in Multiple Models through Inhibition of Glycolysis, the Tricarboxylic Acid Cycle and the igf-1R Pathway," Scientific Reports, Jul. 3, 2017, 7(4537):1-13.
Rouch et al., "Comparison of enteral and parenteral methods of urine alkalinization in patients receiving high-dose methotrexate," Journal of Oncology Pharmacy Practice, 2017, 23(1):3-9.
Silva et al., "The Potential Role of Systemic Buffers in Reducing Intratumoral Extracellular pH and Acid-Mediated Invasion," Cancer Res., Mar. 10, 2009 (online), 69(6):2677-2684.
Ueda et al., "Improvement of aciduria in gout and hyperuricemia, Improvement of Acidosis," Clinical Evaluation, 1981, 9(2):421-433, with partial English translation.
Uralyt, Nippon Chemiphar Co., Ltd., Mar. 8, 2014, with partial English translation.
Zhang et al., "Effect of Citrate on Malignant Pleural Mesothelioma Cells: A Synergistic Effect with Cisplatin," Anticancer Research, Apr. 2009, 29(4):1249-1254.
International Search Report dated Apr. 28, 2020 in PCT/JP2020/004226.

* cited by examiner

*Primary Examiner* — Michael Barker
(74) *Attorney, Agent, or Firm* — Foley & Lardner LLP

(57) ABSTRACT

The present invention relates to a pharmaceutical composition comprising a citrate salt for use in enhancing the effect of an anticancer drug.

20 Claims, 7 Drawing Sheets

(A)

*P<0.05 vs CONTROL (B)

*P<0.05 vs CONTROL (A)

(B)

JULY 23, 2018

ANTICANCER DRUG EFFECT ENHANCER

CROSS-REFERENCE TO RELATED APPLICATIONS

Figure 1:
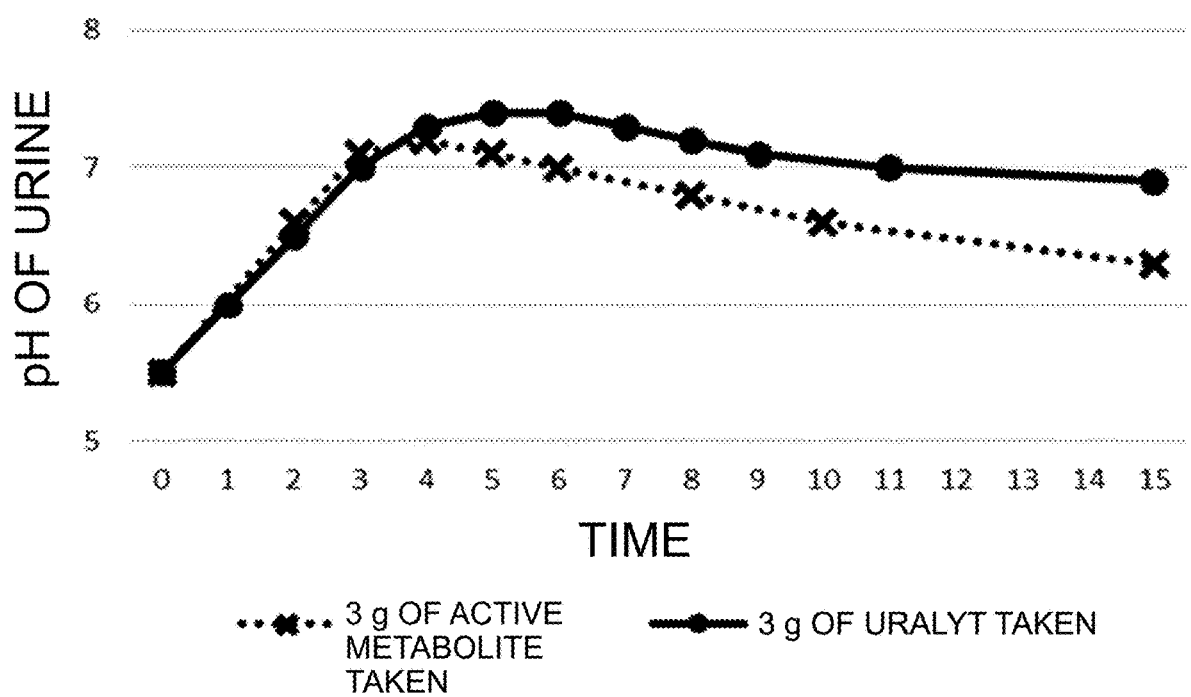

This application is the U.S. National Stage of PCT/JP2020/004226, filed Feb. 5, 2020, which claims priority to JP 2019-132679, filed Jul. 18, 2019.

TECHNICAL FIELD

The present invention relates to an anticancer drug effect enhancer, a method for determining whether the effect is enhanced, and a related medical supply.

BACKGROUND ART

There are not a few cases where conventional anticancer drug treatment mainly aimed at shrinkage of cancer is associated with side effects having a severe impact on health of a cancer patient. Many of cancer molecular target drugs and antibody drugs for cancer immunotherapy are expensive, and that poses a serious social problem for elderly cancer patients and socially vulnerable people and the number of such people has been growing recently.

Development of diagnostic drugs for predicting the effects of cancer immunotherapeutic drugs, cancer molecular target drugs and cancer chemotherapeutic drugs has been advanced in recent years. Those diagnostic drugs have been applied in clinical settings, and are expensive. Thus, medical care costs along with drug costs may continue to more and more increase in the time to come.

Therefore, development of a low-cost and convenient diagnostic method for predicting the therapeutic effects of cancer immunotherapeutic drugs, cancer molecular target drugs and cancer chemotherapeutic drugs, and related medical supplies is desired.

Typically, normal cells have an intracellular pH (hereinafter, referred to as a "pHi") of 6.9 to 7.2 and an extracellular pH (hereinafter, referred to as a "pHe") of 7.3 to 7.4. Thus, normal cells are more alkaline in pHe than in pHi. On the other hand, cancer cells have a pHi of 7.1 to 7.6 and a pHe of 6.2 to 6.9. Thus, cancer cells are more acidic in pHe than in pHi. That is, the pH gradient between pHi and pHe in cancer cells is adverse to that in normal cells. In cancer cells, the glycolytic system is activated, and production of lactic acid and protons (hydrogen ions) is increased as compared to normal cells. The produced lactic acid is actively discharged to outside of the cells by a monocarboxylic acid transporter (MCT), while the produced protons are actively discharge to outside of the cells by a $Na^+/H^+$ exchanger 1 (NHE-1), a $Na^+$-dependent $HCO_3^-/Cl^-$ exchanger and a $H^+$/lactic acid cotransporter. As a result, cancer cells are more acidic in of pHe than in pHi. Studies have been reported which show that in cells having high pHi and increased NHE-1 activity, malignant transformation of cells, cell growth, expression of a cancer gene, activation of growth factors, activation of a glycolytic system, promotion of DNA synthesis, cell cycle activation, depression of apoptosis induction, cell migration, neovascularization, cancer metastasis and drug resistance are enhanced (Non Patent Literature 1).

In addition, in cancer cells, NHE-1 is activated, and thereby formation of pseudopodia and aggregation of lysosomes including proteolytic enzymes at the tip of pseudopodia are promoted. Studies have been reported which show that further activation of NHE-1 turns cancer cells into ameboid, promotes secretion of proteolytic enzymes from localized lysosomes, and makes it easy for cancer cells to infiltrate to outside of tissues, so that growth of cancer cells is facilitated (Non Patent Literature 2).

Heretofore, test-tube studies have been reported which show that cancer cells can be turned from being acidic to being alkaline in pHe to suppress growth and infiltration of cancer cells by increasing the concentration of sodium hydrogencarbonate in serum (Non Patent Literature 3).

Studies have been reported which show that when a cancer immune checkpoint inhibitor such as an anti-PD-1 antibody is intravenously administered to C57B/6 mice implanted with B16 melanoma cells while a sodium hydrogencarbonate aqueous solution (200 mmol/L (17 g/L)) is given to the mice, the antitumor effect in the mice is significantly higher than that in a group of mice treated in the same manner except that only water is given instead of the sodium hydrogencarbonate aqueous solution (Non Patent Literature 4).

Studies have been reported which show that when an mTORC1 inhibitor such as rapamycin is administered to C57B/6 mice implanted with an HT29 human non-small cell lung cancer cell line while a sodium hydrogencarbonate aqueous solution (200 mmol/L (17 g/L)) is given to the mice, the antitumor effect in the mice is significantly higher than that in a group of mice treated in the same manner except that only water is given instead of the sodium hydrogencarbonate aqueous solution (Non Patent Literature 5).

It has been suggested that when a life-extending effect on lung cancer patients by administration of an inhibitor against tyrosine kinase of an epidermal growth factor receptor, such as gefitinib, erlotinib or afatinib, was examined using non-small cell lung cancer patients as subjects with a genetic mutation observed in EGFR (epidermal growth factor receptor), the urine of the cancer patients put on an alkali diet (a diet mainly including fruits and vegetables containing citrate salt, succinate salt, malate salt and the like apt to produce hydrogencarbonate ions in living bodies while having a reduced amount of meat apt to produce uric acid in living bodies) was alkalized to contribute to the life-extending effect (Non Patent Literature 6).

A potassium citrate•sodium citrate hydrate tablet (trade name: Uralyt Tablet (manufactured by Nippon Chemiphar Co., Ltd.)) is easily dissolved in drinking water within the oral cavity, easily swallowed, and thus easily taken even by elderly patients having difficulty of swallowing. The tablet has been widely applied in clinical settings for adaptation to acidosis ameliorating drugs, acidic urine ameliorating drugs for high uric acid blood and acidic urine ameliorating drugs for gout (Non Patent Literatures 7 and 8).

A method for directly measuring a pH change in the microenvironment around cancer cells is not known. Since the blood is kept at a pH of 7.4 (neutral), it is difficult to pharmacokinetically predict a pH change in the microenvironment around cancer cells from a pH change in the blood. Presumption of a pH change in the microenvironment around cancer cells from a pH change in the urine is known (Non Patent Literature 6 and Patent Literature 1), but hardly provides direct evidence of the pH change in the microenvironment around cancer cells.

It is said that the prevalence of cancer is equivalent to one in two people, and the prevalence is further higher in elderly people. Advent of a patient-friendly anticancer drug, diagnostic drug and medical supply are desired.

CITATION LIST

Patent Literature

[Patent Literature 1]
Japanese Patent No. 6359198

Non Patent Literatures

[Non Patent Literature 1]
S. Harguindey et al., Biochimica et Biophysica Acta 1756 (2005): 1-24
[Non Patent Literature 2]
Rosa A. Cardone et al., Nature Reviews, Cancer 5 (2005): 786-795
[Non Patent Literature 3]
Ariosto S. Silva et al., Cancer Research 69 (2009): 2677-2684
[Non Patent Literature 4]
Shari Pilon-Thomas, et al., Cancer Research Science 76 (2016): 1381-1390
[Non Patent Literature 5]
Serlina Faes et al., Molecular Cancer (2016) 15:78
[Non Patent Literature 6]
Reo Hamaguch et al., Anticancer Research 37 (2017): 5141-5145
[Non Patent Literature 7]
Package Insert of Uralyt Tablet (amended in March 2014 (8th edition))
[Non Patent Literature 8]
Yasushi Ueda et al., Rinsho Hyoka 9, 421, 1981

SUMMARY OF INVENTION

Technical Problem

Aging of the population and advancement of healthcare have necessary caused an increase in medical cost, and have placed a heavy burden on patients, and had a major impact on the medical insurance finances of the national and local governments. Accordingly, an object of the present invention is to provide a novel means capable of enhancing the effect of an anticancer drug.

Solution to Problem

The present inventors have extensively conducted studies for solving the above problems, and therefore found that combined administration of a citrate salt and an anticancer drug enhances the effect of the anticancer drug. The present invention is based on these findings.

Accordingly, the present invention includes the followings:

[1] A pharmaceutical composition comprising a citrate salt for use in enhancing an effect of an anticancer drug.
[2] The pharmaceutical composition according to [1], wherein the citrate salt comprises one or more selected from the group consisting of a sodium salt of citric acid, a potassium salt of citric acid, a calcium salt of citric acid, a magnesium salt of citric acid and a solvate thereof.
[3] The pharmaceutical composition according to [1] or [2], wherein the pharmaceutical composition is for oral administration.
[4] The pharmaceutical composition according to any one of [1] to [3], wherein the pharmaceutical composition comprises a combination of potassium citrate and sodium citrate hydrate.
[5] A method for determining a possibility of enhancing the effect of an anticancer drug with a citrate salt, the method comprising:
measuring a concentration of hydrogencarbonate ions in blood or urine of a cancer patient given a citrate salt, and determining that the citrate salt is effective for the patient when the concentration of hydrogencarbonate ions increases; and/or
measuring a pH of urine of the patient, and determining that the citrate salt is effective for the patient when the urine is alkalized in pH.
[6] A method for selecting a patient for whom it is effective to enhance the effect of an anticancer drug with a citrate salt, the method comprising:
measuring a concentration of hydrogencarbonate ions in blood or urine of a cancer patient given a citrate salt, and determining that the citrate salt is effective for the patient when the concentration of hydrogencarbonate ions increases; and/or
measuring a pH of urine of the patient, and determining that the citrate salt is effective for the patient when the urine is alkalized in pH.
[7] A disposal diaper comprising a urine pH test member.
[8] The method according to [5] or [6], further comprising performing cancer treatment by administering the citrate salt and the anticancer drug to the patient for whom the citrate salt is determined to be effective.
[9] The method according to any one of [5], [6] and [8], wherein the citrate salt comprises one or more selected from the group consisting of a sodium salt of citric acid, a potassium salt of citric acid, a calcium salt of citric acid, a magnesium salt of citric acid and a solvate thereof.
[10] The method according to any one of [5], [6], [8] and [9], wherein the administration is oral administration.
[11] The method according to any one of [5], [6], and [8] to [10], wherein the citrate salt is a combination of potassium citrate and sodium citrate hydrate.
[12] A method for treating cancer, the method comprising administering a citrate salt and an anticancer drug to a cancer patient.
[13] The method according to [12], wherein the citrate salt comprises one or more selected from the group consisting of a sodium salt of citric acid, a potassium salt of citric acid, a calcium salt of citric acid, a magnesium salt of citric acid and a solvate thereof.
[14] The method according to [12] or [13], wherein the citrate salt is for oral administration.
[15] The method according to any one of [12] to [15], wherein the citrate salt is a combination of potassium citrate and sodium citrate hydrate.
[16] Use of a citrate salt in production of a medicament for use in a method for enhancing the effect of an anticancer drug.
[17] The use according to [16], wherein the citrate salt comprises one or more selected from the group consisting of a sodium salt of citric acid, a potassium salt of citric acid, a calcium salt of citric acid, a magnesium salt of citric acid and a solvate thereof.
[18] The use according to [16] or [17], wherein the citrate salt is a combination of potassium citrate and sodium citrate hydrate.
[19] A citrate salt for use in a method for enhancing the effect of an anticancer drug.
[20] The citrate salt according to [19], wherein the citrate salt is one or more compound(s) selected from the group consisting of a sodium salt of citric acid, a potassium salt of citric acid, a calcium salt of citric acid, a magnesium salt of citric acid and a solvate thereof.

[21] The citrate salt according to [19] or [20], wherein the citrate salt is a combination of potassium citrate and sodium citrate hydrate.

[22] A combination drug comprising an anticancer drug and a citrate salt.

[23] The combination drug according to [22], wherein the citrate salt comprises one or more selected from the group consisting of a sodium salt of citric acid, a potassium salt of citric acid, a calcium salt of citric acid, a magnesium salt of citric acid and a solvate thereof.

[24] The combination drug according to [22] or [23], wherein the citrate salt is a combination of potassium citrate and sodium citrate hydrate.

[25] A combination medicament comprising an anticancer drug and a citrate salt.

[26] The combination medicament according to [25], wherein the citrate salt comprises one or more selected from the group consisting of a sodium salt of citric acid, a potassium salt of citric acid, a calcium salt of citric acid, a magnesium salt of citric acid and a solvate thereof.

[27] The combination medicament according to [25] or [26], wherein the citrate salt is a combination of potassium citrate and sodium citrate hydrate.

This specification includes the contents of the specification and/or the drawings of Japanese Patent Application No. 2019-132679 based on which priority to the present application is claimed.

All publications, patents and patent applications cited in this specification are incorporated herein by reference in their entirety.

Advantageous Effects of Invention

According to the present invention, it is possible to provide a novel means capable of enhancing the effect of an anticancer drug. In addition, according to the present invention, it is possible to provide a method for determining a possibility of enhancing the effect of an anticancer drug with a citrate salt, and a medical supply which can be used for the determination and the like.

DESCRIPTION OF EMBODIMENTS

FIG. 1 shows a graph chart showing a time-dependent change in pH of urine collected from an elderly man with aciduria (70 years old) after he took 3 g of a potassium citrate•sodium citrate hydrate combination tablet (referred to as "Uralyt") or 3 g of a sodium salt of hydrogencarbonate ions as an active metabolite of potassium citrate•sodium citrate hydrate.

Figure 2:
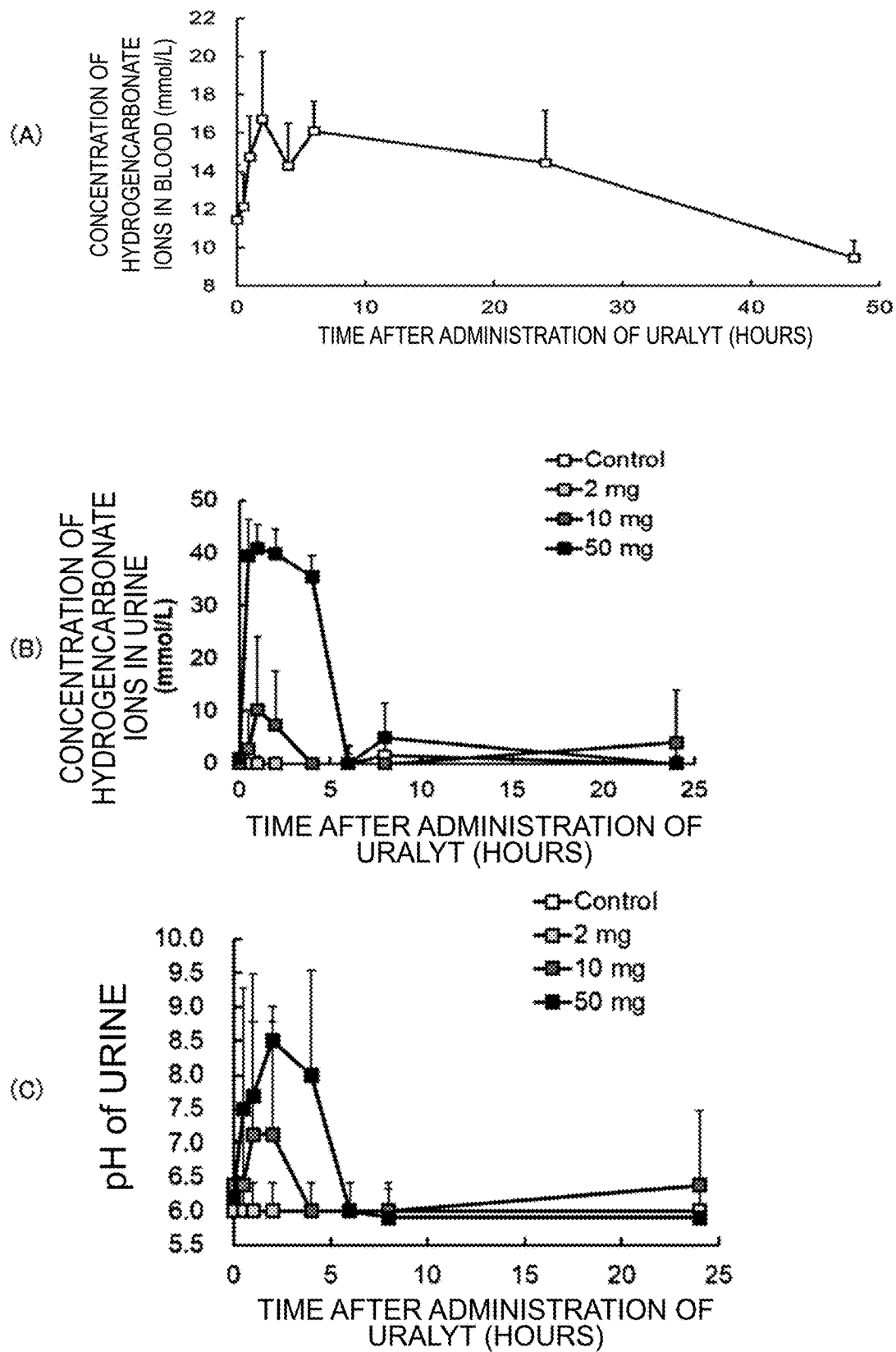

FIG. 2 shows graphic charts showing (A) a change in a concentration of hydrogencarbonate ions in blood as an active metabolite of potassium citrate•sodium citrate hydrate, (B) a change in a concentration of the hydrogencarbonate ions in urine and (C) a change in pH of urine when a potassium citrate•sodium citrate hydrate combination powder (referred to as "Uralyt") was orally administered to a cancer-bearing mouse.

Figure 3:
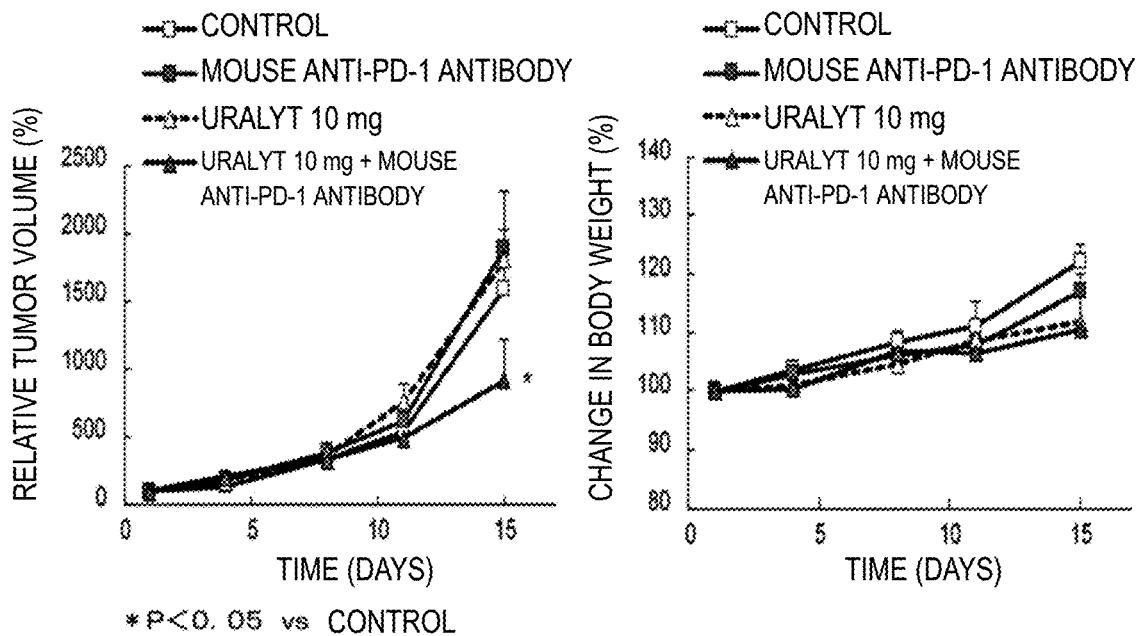
Figure 3:
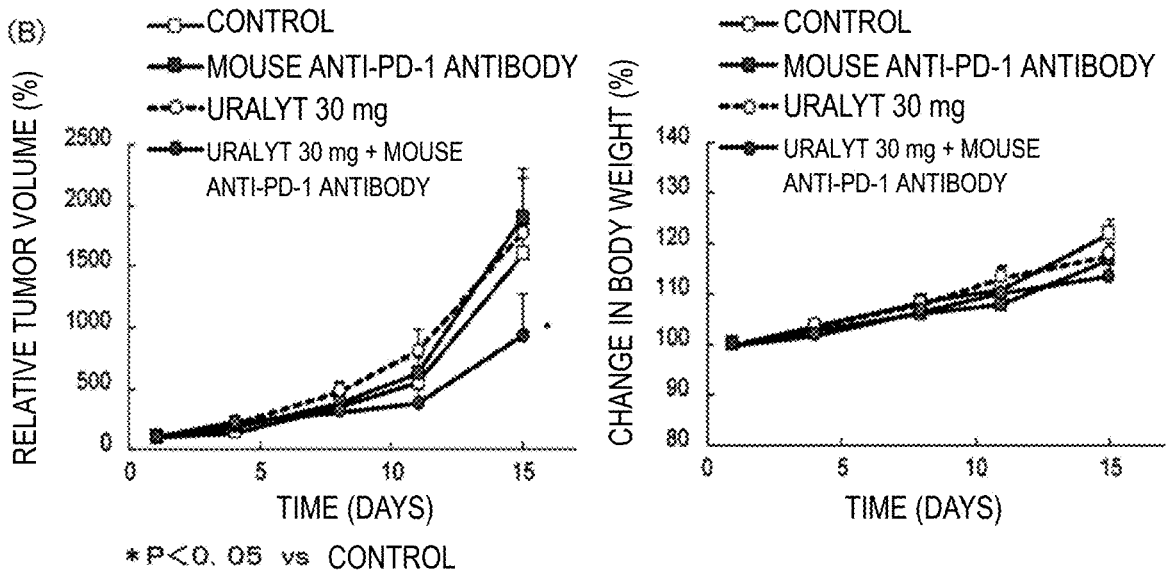

FIG. 3 shows graphic charts showing an inhibitory effect on tumor growth and a change in body weight after (1) a mouse anti-PD-1 antibody (5 mg/kg), (2) a potassium citrate•sodium citrate hydrate combination powder (referred to as "Uralyt") (10 mg/day or 30 mg/day/mouse (oral)) or (3) a mouse anti-PD-1 antibody (5 mg/kg) and a potassium citrate•sodium citrate hydrate combination powder (10 mg/day or 30 mg/day/mouse (oral)) was administered to a cancer-bearing mouse (model subcutaneously implanted with a B16 mouse melanoma cell line), where FIG. 3(A) shows the results of administering Uralyt at 10 mg/day/mouse, and FIG. 3(B) shows the results of administering Uralyt at 30 mg/day/mouse.

Figure 4:
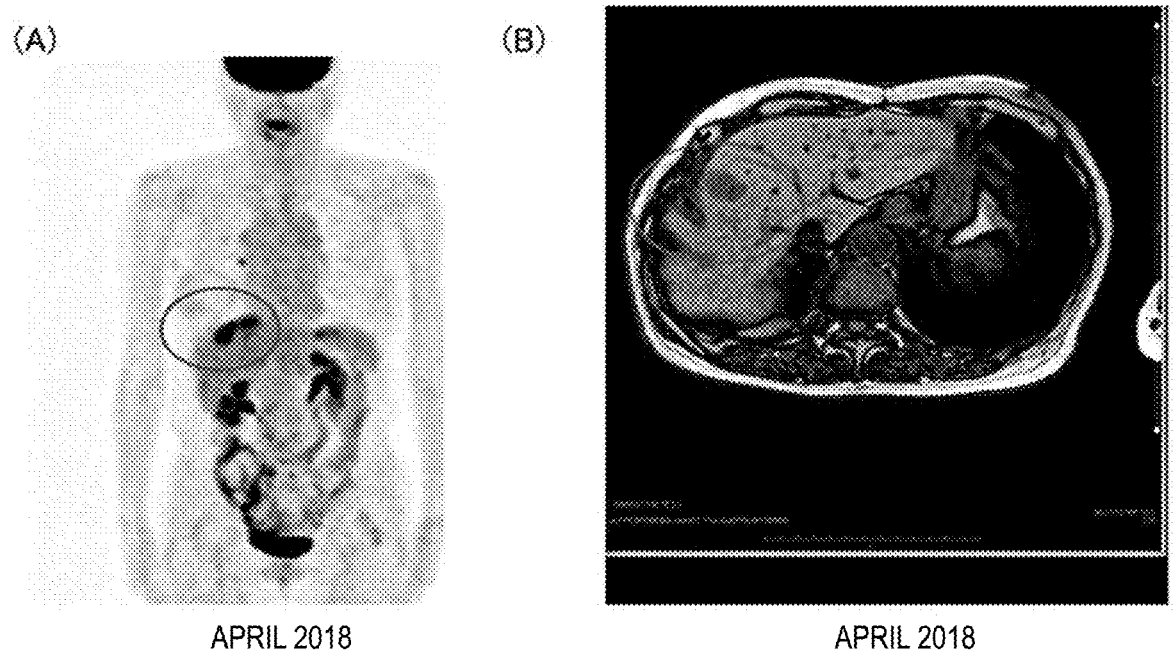

FIG. 4 shows photographic charts showing (A) a PET image (positron emission tomography) and (B) a CT image (computed tomography) taken in April 2018 for a patient having pancreas cancer with liver metastasis (83-year-old woman), who received combined therapy with gemcitabine (trade name: Gemzar (Eli Lilly and Company)) and nab-taxel (trade name: Abraxane (TAIHO Pharmaceutical Co., Ltd.)) as standard therapy for pancreas cancer, but gave up halfway because of side effects.

Figure 5:
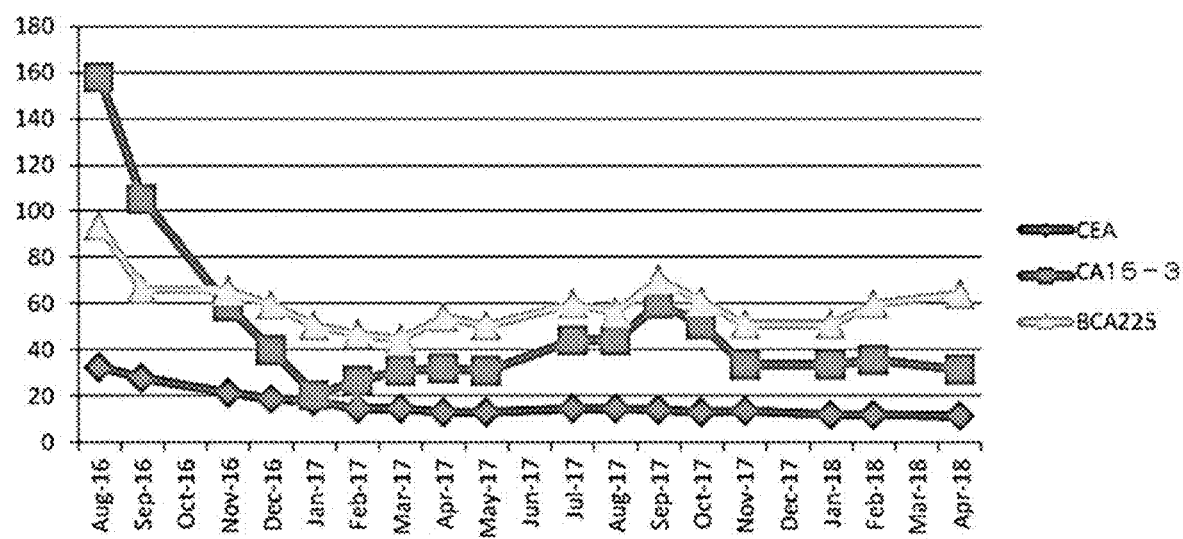

FIG. 5 shows a graphic chart showing the measured values of blood tumor markers (CEA, CA15-3 and BCA225) for a breast cancer patient (54-year-old woman) who received daily oral administration (20 mg/day) of tamoxifen citrate (trade name: Tasuomin (Bayer Yakuhin, Ltd.)) and daily oral administration (15 g/day) of a sodium salt of hydrogencarbonate ions as an active metabolite of potassium citrate•sodium citrate hydrate from June 2016.

Figure 6:
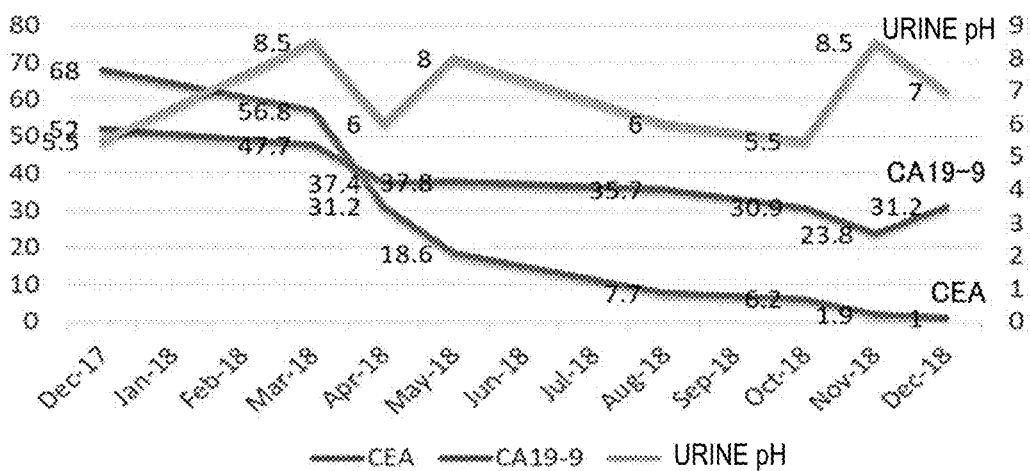

FIG. 6 shows a graphic chart showing a change in pH of urine and a change in levels of tumor markers (CEA and CA19-9) when standard chemotherapy for colorectal cancer (FOLFOX+Bev) and a sodium salt of hydrogencarbonate ions as an active metabolite of potassium citrate•sodium citrate hydrate (10 g/day) were daily administered to a patient having stage IV sigmoid colon cancer with multiple lung metastasis and carcinomatous peritoneum inflammation (40-year-old woman).

Figure 7:
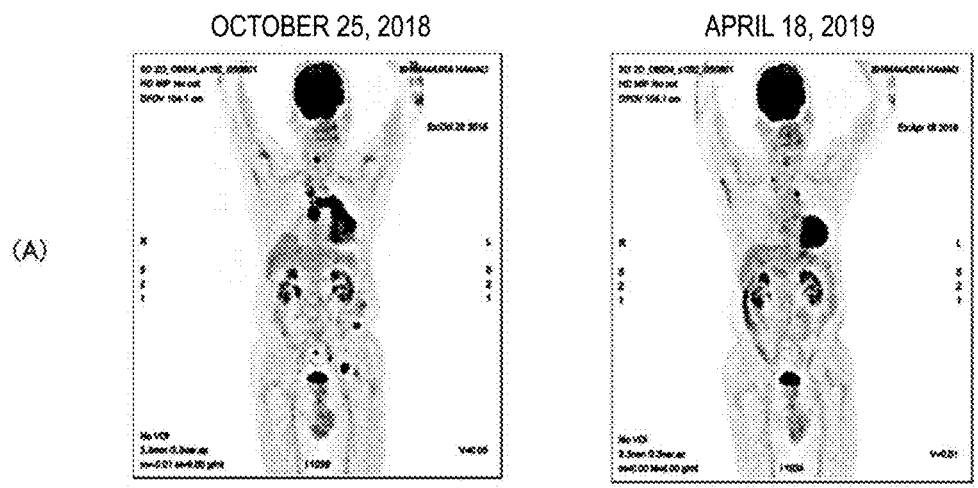
Figure 7:
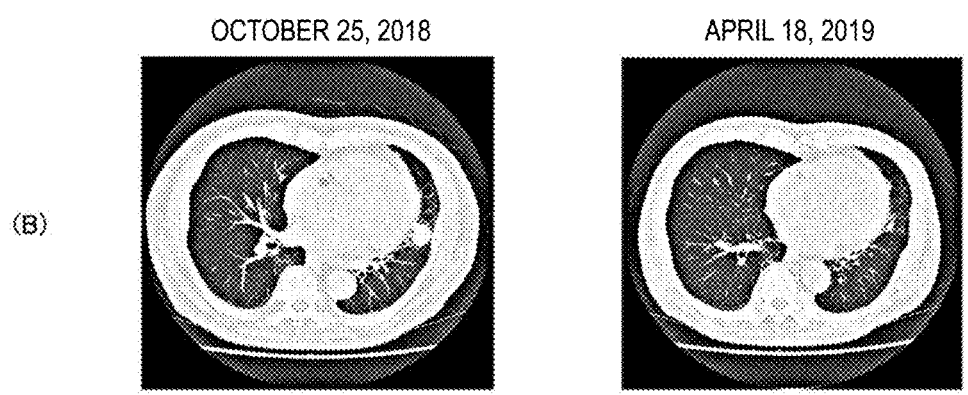

FIG. 7 shows photographic charts showing (A) PET images and (B) CT images of a lung part before and after treatment in which a patient having stage IVB non-small cell lung cancer (adenocarcinoma) with hilar and mediastinal lymph node metastasis and multiple bone metastasis (87-year-old man) received daily administration of a sodium salt of hydrogencarbonate ions as an active metabolite of potassium citrate•sodium citrate hydrate (10 g/day) and biweekly oral administration of one capsule of 100 mg UFT for about a month (dose equal to or less than one-fifth of the normal dose).

Figure 8:
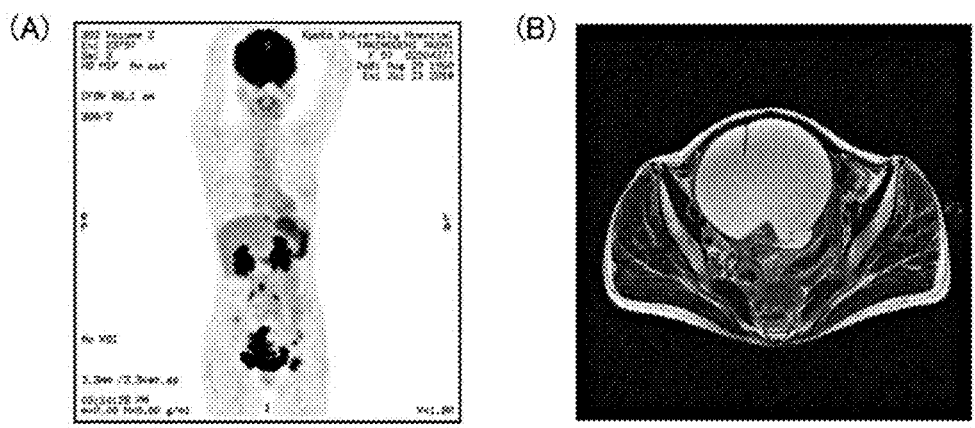
Figure 8:
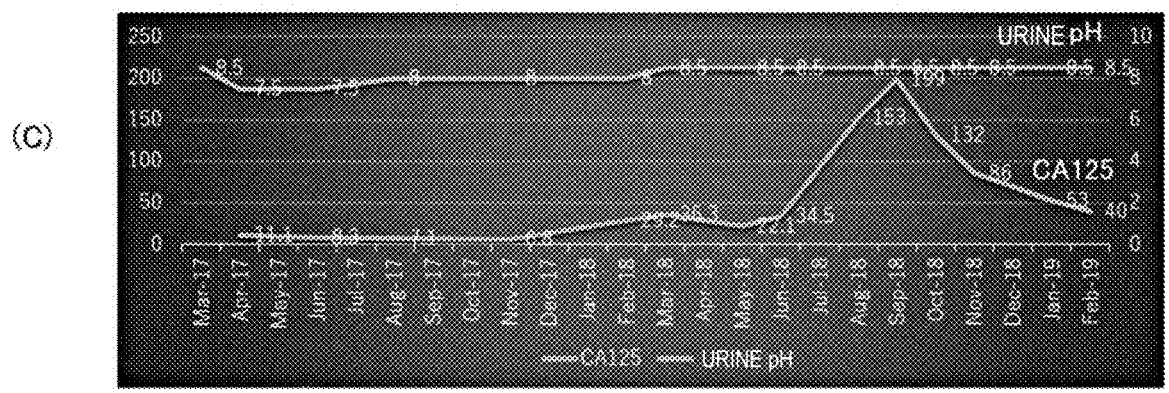

FIG. 8 shows photographic charts showing (A) a PET image and (B) a CT image taken on Jul. 23, 2018 for a patient having stage IVB terminal ovarian cancer (57-year-old woman). FIG. 8 (C) shows a graphic chart showing the measured values of the urine pH and the blood tumor marker (CA125) level before and after treatment started in August 2018, where a sodium salt of hydrogencarbonate ions as an active metabolite of potassium citrate•sodium citrate hydrate was daily administered (15 g/day) and an endoxan (equivalent to a fraction of the normal dose) was biweekly administered at 50 mg tablet/day.

Figure 9:
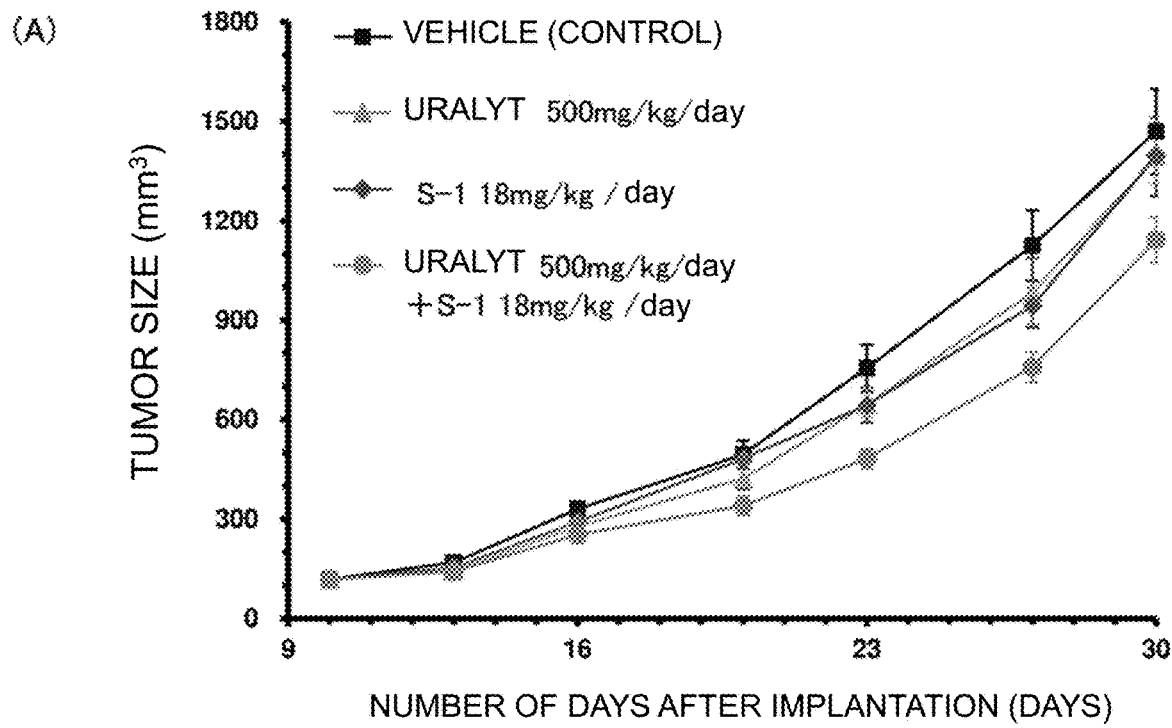
Figure 9:
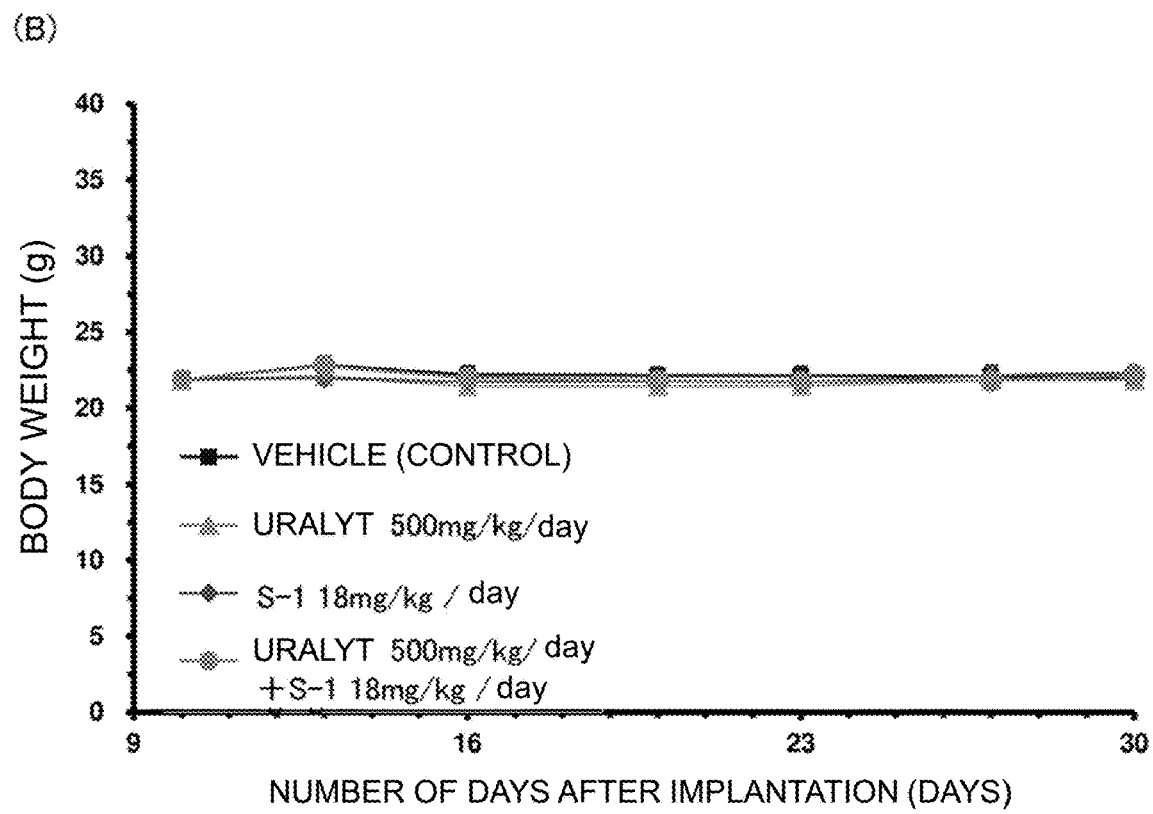

FIG. 9 shows graphic charts showing (A) a change in tumor size (suppression of tumor growth) and (B) a change in body weight after a vehicle (control), a potassium citrate•sodium citrate hydrate combination powder (referred to as "Uralyt") (500 mg/kg/day (oral)), a tegafur•gimeracil•oteracil potassium combination drug (referred to as "S-1") (18 mg/kg/day (oral)) and a combination of S-1 (18 mg/kg/day (oral administration)) and Uralyt (500 mg/kg/day (oral)) were each administered to a cancer-bearing mouse (model obtained by subcutaneously implanting a mouse with a PANC-1 human pancreas cancer cell line).

DESCRIPTION OF EMBODIMENT

The present invention relates to a pharmaceutical composition containing a citrate salt for use in enhancing the effect of an anticancer drug.

In the present invention, "enhancing the effect of an anticancer drug" means that anticancer activity of an anticancer drug is enhanced by 20% or more, 30% or more, 40% or more, 50% or more, 60% or more, 70% or more, 80% or more or 90% or more as compared to a case where the anticancer drug is used alone. The "anticancer activity" not only means that cancer is completely eliminated, but also means that cancer is temporarily or permanently shrunk or eliminated, or cancer is stabilized without progression. Examples of the effect provided by anticancer activity include one or more of reduction in cancer size, reduction in tumor marker level, amelioration of a symptom associated with cancer, extension of a scale such as an overall survival period, a progression-free survival period or a median overall survival period. By "enhancing the effect of an anticancer drug", the anticancer drug can be administered at a reduced dose equal to 90%, 80%, 70%, 60%, 50%, 40% or lower of the dose of the anticancer drug used alone, and/or in accordance with a regimen with a reduced administration period and/or an extended non-dosing period. Accordingly, development of side effects which can be caused by administration of an anticancer drug (examples include, but are not limited to, bone-marrow suppression, hemolytic anemia, disseminated intravascular coagulation syndrome, fulminant hepatitis, symptom of dehydration, bowel inflammation, interstitial pneumonia, mouth inflammation, gastrointestinal tract ulcer, gastrointestinal hemorrhage, gastrointestinal perforation, acute renal failure, mucocutaneous ocular syndrome, toxic epidermal necrosis, psychoneurotic disorder, acute pancreatitis, rhabdomyolysis and lost sense of smell) can be suppressed or retarded, and an economic burden on cancer patients and a burden on the medical insurance finances of the national and local governments can be considerably reduced.

In the present invention, examples of the "cancer" include, but are not limited to, blood cancers (e.g. acute myeloid leukemia, chronic myeloid leukemia, malignant lymphoma and multiple myeloma), solid cancers (e.g. brain cancer/glial tumor, pituitary adenoma, acoustic schwannoma, uveal malignant melanoma, meningeal tumor, throat cancer, larynx cancer, carcinoma linguae, thyroid cancer, breast cancer, lung cancer, thymoma, thymic cancer, mesothelioma, esophageal cancer, stomach cancer, bowel cancer, hepatocellular cancer, bile duct cancer, pancreas cancer, renal cellular cancer, bladder cancer, prostate cancer, kidney pelvis/ureter cancer, penis cancer, testicular (testicle) cancer, uterus cancer, ovarian cancer, vulva cancer, skin cancer, malignant melanoma (skin), basal cell cancer, prodromal symptoms of skin cancer, intraepidermal cancer, squamous cell cancer, mycosis fungoides, malignant bone tumor (bone sarcoma), soft tissue sarcoma, chondrosarcoma and malignant fibrous histiocytoma), and metastatic cancers thereof.

In the present invention, the "anticancer drug" is not particularly limited as long as the anticancer drug is used in treatment of cancer, and examples thereof include cancer immunotherapeutic drugs, cancer molecular target drugs and cancer chemotherapeutic drugs. More specific examples include, but are not limited to, tegafur, tegafur•uracil combination drug (trade name: UFT), tegafur•gimeracil•oteracil potassium combination drug (trade name: TS-1®), fluorouracil, gemcitabine (trade name: Gemzar®), enocitabine, carmofur, doxifluridine, cytarabine, cytarabine ocfosfate, mercaptopurine, fludarabine, capecitabine, methotrexate, cladribine, pemetrexed (trade name: Alimta®), hydroxycarbamide, cyclophosphamide, thiotepa, ifosfamide, busulfan, dacarbazine, melphalan, ranimustine, nimustine, temozolomide, carboplatin, cisplatin, oxaliplatin, nedaplatin, doxorubicin, aclarubicin, idarubicin, actinomycin D, daunorubicin, zinostatin stimalamar, bleomycin, mitomycin C, pirarubicin, epirubicin, peplomycin, amrubicin, *vinca* alkaloid, a topoisomerase inhibitor, sorafenib, erlotinib, axitinib, everolimus, sunitinib, imatinib, lapatinib, rituximab, dasatinib, bortezomib, tamibarotene, gefitinib, ibritumomab, nilotinib, temsirolimus, trastuzumab, panitumumab, tretinoin, gemtuzumab ozogamicin, crizotinib, afatinib, bevacizumab (trade name: Avastin®), paclitaxel (trade name: Abraxane®), docetaxel (trade name: Taxotere®), nivolumab (trade name: Opdivo®), pembrolizumab (trade name: Keytruda®), ipilimumab (trade name: Yervoy®), atezolizumab (trade name: Tecentriq®), [2S]-2-[(2S,3R)-3-amino-2-hydroxy-4-phenylbutanoylamino]-4-methylpenanoic acid (general name: Ubenimex) (trade name: Bestatin), and lentinan. The anticancer drug is preferably a cancer immunotherapeutic drug, particularly preferably nivolumab (trade name: Opdivo®), pembrolizumab (trade name: Keytruda®), ipilimumab (trade name: Yervoy®) or atezolizumab (trade name: Tecentriq®).

In the present invention, the "citrate salt" is one selected from the group consisting of a sodium salt of citric acid, a potassium salt of citric acid, a calcium salt of citric acid, a magnesium salt of citric acid, and a solvate thereof, or a combination of two or more thereof. In the present invention, the "citrate salt" is preferably a combination of potassium citrate and sodium citrate hydrate.

The pharmaceutical composition according to the present invention may contain, in addition to the above citrate salt, an excipient, a binding agent, a disintegrant, a lubricant and the like which are commonly used in production of medicaments. The pharmaceutical composition can be produced as a dosage form suitable for an intended administration route.

Examples of the excipient include sugars (monosaccharides, disaccharides, and polysaccharides such as cyclodextrin and alginic acid), metal salts, kaolin, silicic acid, polyethylene glycol, and mixtures thereof.

Examples of the binding agent include simple syrup, glucose solutions, starch solutions, gelatin solutions, polyvinyl alcohol, polyvinyl ether, polyvinyl pyrrolidone, carboxymethylcellulose, shellac, methylcellulose, ethylcellulose, and mixtures thereof.

Examples of the disintegrant include dry starch, sodium alginate, agar powder, laminaran powder, sodium hydrogencarbonate, calcium carbonate, polyoxyethylene sorbitan fatty acid esters, sodium lauryl sulfate, monoglyceride stearate, starch, lactose, and mixtures thereof.

Examples of the lubricant include purified talc, stearates, borax, polyethylene glycol, and mixtures thereof.

If necessary, the pharmaceutical composition may appropriately contain a diluent, a stabilizing agent, a tonicity agent, a pH adjuster, a buffer, a solubilizing agent, a suspending agent, a colorant, a flavoring agent, a deodorant, a coating agent, a preserving agent, an antiseptic agent, an antioxidant and the like which are commonly used in production of medicaments.

When the citrate salt is a combination of two or more components (for example, a combination of potassium citrate and sodium citrate hydrate), each of these components may be provided in separate pharmaceutical composition forms, or provided in a combination medicament form.

When these components are provided as separate pharmaceutical compositions, these pharmaceutical compositions are intended to be used in combined administration, and the package inserts thereof may inform the user accordingly in the column of "Effect and Efficacy" or "Dosage and Administration". In the present invention, the "combined administration" means not only the case where the components are administered in parallel, but also the case where the components are sequentially administered at their respective predetermined intervals, over a treatment period (combination therapy). The administration routes as well as the administration means for the components administered in combination may be the same or different. In the case of, for example, the combination of potassium citrate and sodium citrate hydrate described above, the package insert of the pharmaceutical composition including potassium citrate may indicate that "the pharmaceutical composition is administered in combination with sodium citrate hydrate" for enhancing the effect of an anticancer drug or treating cancer with an anticancer drug, and the package insert of the pharmaceutical composition including sodium citrate hydrate may indicate that "the pharmaceutical composition is administered in combination with potassium citrate" for enhancing the effect of an anticancer drug or treating cancer with an anticancer drug.

When the components are provided in a combination medicament form, the components may be provided in a combination drug form with one composition containing the components, or the components may be separately prepared, and turned into a form in which the components are produced, packaged and distributed as a single package suitable for combined administration (that is, a kit preparation). In the case of, for example, the combination of potassium citrate and sodium citrate hydrate described above, the combination medicament can take a combination drug form containing these components. In the present invention, a commercially available combination drug may be used, and for example, Uralyt® (manufactured by Nippon Chemiphar Co., Ltd.) can be suitably used.

The dose and the administration route of the citrate salt can vary depending on the type and the severity of cancer, and the age, the body weight and the condition of a patient. The citrate can be administered through any administration route (oral administration or parenteral administration) in an amount sufficient to ensure that the pH value of the urine in a dosed patient is on the more alkaline side than the pH value of the urine before administration, preferably the pH value of the urine in the dosed patient is kept neutral or alkaline, and/or the citrate can be administered through any administration route (oral administration or parenteral administration) in an amount sufficient to make the concentration of an active metabolite of the citrate salt (hydrogencarbonate ions in the case of, for example, the combination of potassium citrate and sodium citrate hydrate described above) in the blood or urine in the dosed patient higher than that before administration.

For example, the citrate salt (when a plurality of components are present, each of the components) can be orally administered every day, every other day or every few days once to five times (twice or three times) a day at a daily dose selected from the range of 100 mg to 10 g, preferably the range of 150 mg to 5 g, more preferably the range of 200 mg to 2 g. In the case of, for example, the combination of potassium citrate and sodium citrate hydrate described above, the combination drug (e.g. Uralyt® (manufactured by Nippon Chemiphar Co., Ltd.)) can be orally administered every day, every other day or every few days once to five times (twice or three times) a day at a daily dose selected from the range of 1 to 20 g, preferably the range of 1 to 10 g, more preferably the range of 1 to 5 g.

In the present invention, the citrate salt can be used for enhancing the effect of an anticancer drug administered in combination. It is considered that the citrate salt administered to a cancer patient changes the microenvironment around cancer cells to make cancer cells more sensitive to the anticancer drug, so that the effect of the anticancer drug is enhanced. It is not easy to directly measure a change in the microenvironment around cancer cells, but a change in the microenvironment can be confirmed by reference to a change in a concentration of an active metabolite of the citrate salt (a change in a concentration of hydrogencarbonate ions in the case of, for example, the combination of potassium citrate and sodium citrate hydrate described above) in the blood or urine of the cancer patient given the citrate salt. Additionally or alternatively, such a change in the microenvironment can be confirmed by reference to a change in pH value of the urine of the cancer patient given the citrate salt. When the sample is blood, measurement is performed within approximately 36 hours, preferably within approximately 24 hours, more preferably within 12 hours, still more preferably within 6 hours after administration of the citrate salt. When the sample is urine, measurement is performed within approximately 12 hours, more preferably within 6 hours, still more preferably within 3 hours after administration of the citrate salt.

Thus, when the result of measuring a concentration of an active metabolite of the citrate salt (hydrogencarbonate ions in the case of, for example, the combination of potassium citrate and sodium citrate hydrate) in the blood or urine of an intended cancer patient after administrating the citrate salt to the patient shows that the concentration is higher than that before administration of the citrate salt, a change in the microenvironment around cancer cells can occur. That is, for the patient, administration of the citrate salt in combination can be expected to enhance the effect of the anticancer drug. When the result of measuring the value of urine pH of the patient after administrating the citrate salt shows that the value of urine pH is on the more alkaline side than that before administration of the citrate salt, preferably the urine in the dosed patient is neutral or alkaline in pH value, a change in the microenvironment around cancer cells can occur. That is, for the patient, administration of the citrate salt in combination can be expected to enhance the effect of the anticancer drug.

In this way, it is possible to easily select a cancer patient for whom administration of the citrate salt in combination can be expected to enhance the effect of the anticancer drug, and after selection of a relevant patient, cancer treatment based on combined administration of the citrate salt and the anticancer drug can be performed on the patient. When administered in combination with the citrate salt, the anticancer drug can be administered at a reduced dose equal to 90%, 80%, 70%, 60%, 50%, 40% or lower of the dose of the anticancer drug used alone, and/or in accordance with a regimen with a reduced administration period and/or an extended non-dosing period, as described above. For example, the anticancer drug can be used in accordance with a dosage regimen which ensures that the immune function of the dosed cancer patient is maintained or is not declined markedly (e.g. by 40% or more, 50% or more, 60% or more, 70% or more, or a higher percentage). A change in immunity of the cancer patient can be determined on the basis of a change in one or more of the values of the number of neutrophils, the number of granulocytes, the number of monocytes, the number of lymphocytes, the number of platelets and the like, preferably the number of lymphocytes.

According to the present invention, combined use of an anticancer drug (e.g. a cancer immunotherapeutic drug such as an anti-PD-1 antibody or an anti-PDL-1 antibody, a cancer molecular target drug or a cancer chemotherapeutic drug) with a citrate salt (e.g. a combination of potassium citrate and sodium citrate hydrate) enables inhibition or suppression of one or more mechanisms related to malignant transformation, growth and metastasis of cancer, such as malignant transformation of cells, growth of cells, expression of a cancer gene, activation of growth factors, activation of a glycolytic system, promotion of DNA synthesis, cell cycle activation, depression of apoptosis induction, cell migration, neovascularization, cancer metastasis and drug resistance, in a cancer patient. Accordingly, the cancer can be calmed, treated or relieved, or recurrence or metastasis can be prevented. In particular, the effect thereof is marked in refractory (progressive and/or terminal) cancer, and the survival probability of the patient can be considerably increased.

The citrate salt according to the present invention is itself effective for treatment or relief of cancer, or prevention of recurrence and metastasis of cancer, and enables considerable reduction of an economic burden on cancer patients and a burden on the medical insurance finances of the national and local governments when used in combination of an anticancer drug.

The present invention also relates to a medical supply for measuring the pH value of urine. The medical supply according to the present invention is in the form of a disposal diaper (e.g. a paper diaper) including a urine pH test member. The "urine pH test member" is a member including a means for measuring the pH value of urine, and can be disposed on a portion of the diaper which receives urine (e.g. a urine pad or water-absorbing material). The "means for measuring the pH value of urine" may be one capable of measuring the pH value of urine, and is not particularly limited, and for example, a substance which displays a specific color depending on a pH value (a pH indicator) can be used. Examples of the pH indicator include, but are not limited to, methyl orange, phenolphthalein and BTB, and one of these substances, or a combination of two or more thereof can be used. Alternatively, a pH test strip can be used as the "means for measuring the pH value of urine".

With the medical supply according to the present invention, the pH value of urine can be measured by observing the "urine pH test member" after the wearer passes urine, acidic urine can be diagnosed, and whether or not the urine is alkalized in pH value after administration of the citrate salt described above can be determined.

EXAMPLES

The present invention will be described in more detail by way of Examples, which should not be construed as limiting the present invention.

[Example 1] Change in pH of Urine Due to Administration of Citrate Salt

A citrate salt was administered to a man (70 years old) with acidic urine in accordance with the following dosage regimen, and a change in pH value of urine was then measured over time.

(Dosage and Administration)

(1) A potassium citrate•sodium citrate hydrate 500 mg tablet (Uralyt Tablet (manufactured by Nippon Chemiphar Co., Ltd.)) is administered at 6 tablets (3 g) once a day after a meal.

(2) A sodium salt of hydrogencarbonate ions as a main active metabolite of potassium citrate•sodium citrate hydrate (500 mg sodium bicarbonate tablet "Mylan" (Mylan Seiyaku Ltd.)) is administered at 6 tablets (3 g) once a day after a meal.

(Results)

FIG. 1 shows the results of measuring the pH of urine after administration of the citrate salt. By orally administering the potassium citrate•sodium citrate hydrate 500 mg tablet (Uralyt Tablet (manufactured by Nippon Chemiphar Co., Ltd.)) at 6 tablets (3 g) once a day after a meal, the urine was alkalized in pH and kept alkaline.

On the other hand, when the sodium bicarbonate 500 mg tablet (Mylan Seiyaku Ltd.) corresponding to a sodium salt of hydrogencarbonate ions as a main active metabolite of potassium citrate•sodium citrate hydrate was administered at 6 tablets (3 g) once a day after a meal, the rate of alkalization was higher, and the rate of turning acidic again was also higher, and the time during which the urine was kept alkaline was shorter, resulting in a poorer ability to keep the urine alkaline, as compared to the case where the potassium citrate•sodium citrate hydrate was administered. In addition, when the sodium salt of hydrogencarbonate ions was administered, the patient often burped.

[Example 2] Change in Concentration of Hydrogencarbonate Ions in Blood and Urine Due to Administration of Citrate Salt 50 mg of potassium citrate•sodium citrate hydrate powder (Uralyt-U combination powder (Nippon Chemiphar Co., Ltd.)) was orally administered to a mouse for implanting cancer cells, and the concentration of an active metabolite (hydrogencarbonate ions) of potassium citrate•sodium citrate hydrate in the blood was measured over time. FIG. 2(A) shows the results.

In addition, the concentration of the active metabolite (hydrogencarbonate ions) of potassium citrate•sodium citrate hydrate in the urine and the pH of the urine of the same mouse after administration were measured over time. FIGS. 2(B) and 2(C) show the results, respectively.

The above results show that a change in a concentration of the active metabolite (hydrogencarbonate ions) of potassium citrate•sodium citrate hydrate in the urine was well liked to a change in pH of the urine, and that while the concentration of the active metabolite (hydrogencarbonate ions) of potassium citrate•sodium citrate hydrate in the blood was lower (by about 40%) than the concentration of the active metabolite (hydrogencarbonate ions) of potassium citrate•sodium citrate hydrate in the urine, the duration of the concentration of hydrogencarbonate ions in the blood is several times longer than the duration of the concentration of hydrogencarbonate ions in the urine.

The concentrations of hydrogencarbonate ions in the blood and in the urine were measured with DIA COLOR (hydrogencarbonate ion concentration measuring kit) from TOYOBO CO., LTD. The pH of the urine was measured with a pH test strip manufactured by Toyo Roshi Kaisha, Ltd.

[Example 3] Enhancing Effect on Anticancer Drug by Administration of Citrate Salt A cancer-bearing mouse (model subcutaneously implanted with B16 mouse melanoma cells) was caused to receive (1) administration of a mouse anti-PD-1 antibody (Bio X Cell, BE0146) (5 mg/kg), (2) administration of a potassium citrate•sodium citrate hydrate combination powder (Uralyt-U combination powder (Nippon Chemiphar Co., Ltd.)) (10 mg/day or 30 mg/day/mouse (oral)), or (3) combined administration of the mouse anti-PD-1 antibody (5 mg/kg) and the potassium citrate•sodium citrate hydrate combination powder (Uralyt-U combination powder (Nippon Chemiphar Co., Ltd.)) (10 mg/day or 30 mg/day/mouse (oral)), and the tumor volume and the body weight of the mouse were measured over time. The potassium citrate•sodium citrate hydrate was administered every day, and the anti-PD-1 antibody was intraperitoneally administered only once at a dose of 5 mg/kg/day on the day following the day of the cell implantation (Day 1).

FIGS. 3(A) and 3(B) show a relative tumor volume (%) (inhibitory effect on tumor growth) and a change in body weight (%). When the potassium citrate•sodium citrate hydrate was administered daily at 30 mg/day, and when the potassium citrate•sodium citrate hydrate was administered daily at 10 mg/day, both cases showed that the anticancer effect of the anti-PD-1 antibody in a mouse subcutaneously implanted with B16 mouse melanoma cells was enhanced. This result shows that the potassium citrate•sodium citrate hydrate can serve as an effect enhancer for Opdivo (anti-PD-1 antibody) and Keytruda (anti-PDL-1 antibody) which have had a limitation in treatment of cancer patients because the drug expense is high and the effect is not sufficient.

Examples 4 to 8 below show an enhancing effect on an anticancer drug by combined use of the anticancer drug and potassium citrate•sodium citrate hydrate (hereinafter, a sodium salt of hydrogencarbonate ions as an active metabolite thereof is used), which was confirmed in actual cancer patients.

[Example 4] Enhancing Effect on Anticancer Drug in Pancreas Cancer Patient

A patient having pancreas cancer with liver metastasis (83-year-old woman) received combined therapy with gemcitabine (trade name: Gemzar (Eli Lilly and Company)) and nab-taxel (trade name: Abraxane (TAIHO Pharmaceutical Co., Ltd.)) as standard therapy for pancreas cancer, but gave up halfway in the treatment because of side effects. As shown in a PET image (positron emission tomography) and a CT image (computed tomography) taken in April 2018, the patient was placed in a harsh state with a tumor observed in the liver (FIGS. 4(A) and 4(B)).

Thereafter, the above-mentioned standard therapy was replaced by combined administration of Gemzar in an amount equal to one-third of the normal amount and a sodium salt of hydrogencarbonate ions as an active metabolite of potassium citrate•sodium citrate hydrate (10 g/day). Only 3 months after the start of the combined administration, the level of CA19-9 as a tumor marker for pancreas cancer decreased (150→50), and thereafter continued to decrease. The urine was kept alkaline with the pH being 7.5 to 8.5. This patient did not receive either high-dose vitamin C instillation therapy or oral administration of metformin as a diabetes drug.

[Example 5] Enhancing Effect on Anticancer Drug in Breast Cancer Patient

A breast cancer patient (54-year-old woman), who underwent removal of a part of the left breast in July 2001 and had recurrent breast cancer with induced carcinomatous pleurisy in August 2011, received daily administration (20 mg/day) of tamoxifen citrate (trade name: Tasuomin (Bayer Yakuhin, Ltd.)) and daily administration (15 g/day) of a sodium salt of hydrogencarbonate ions as a citrate metabolite of potassium citrate•sodium citrate hydrate from June 2016.

As a result, the urine was kept alkaline with the pH falling within the range of 7.5 to 8.5, and the levels of CEA, CA15-3 and BCA225 as blood tumor markers continued to decrease over a year and a half or more (FIG. 5). This patient did not receive any of chemotherapy commonly applied to progressive recurrent breast cancer, high-dose vitamin C instillation therapy and oral administration of metformin as a diabetes drug.

[Example 6] Enhancing Effect on Anticancer Drug in Colon Cancer Patient

From December 2017, standard chemotherapy for colorectal cancer (FOLFOX+Bev) and a sodium salt of hydrogencarbonate ions as an active metabolite of potassium citrate•sodium citrate hydrate (10 g/day) were daily administered to a patient having stage IV sigmoid colon cancer recurring after the operation and involving multiple lung metastasis and carcinomatous peritoneum inflammation (40-year-old woman). FIG. 6 shows a change in pH of the urine of the patient and a change in levels of tumor markers (CEA and CA19-9) during this treatment period. The urine was alkalized in pH, and the levels of CEA and CA19-9 as tumor markers both decreased. In addition, the CT image of the lung also showed that the multiple lung metastasis turned down. This patient did not receive either high-dose vitamin C instillation therapy or oral administration of metformin as a diabetes drug.

[Example 7] Enhancing Effect on Anticancer Drug in Non-Small Cell Lung Adenocarcinoma Patient A patient having stage IVB non-small cell lung adenocarcinoma with hilar and mediastinal lymph node metastasis and multiple bone metastasis (87-year-old man) received daily administration of a sodium salt of hydrogencarbonate ions as a metabolite of potassium citrate•sodium citrate hydrate (10 g/day) and biweekly oral administration of one capsule of 100 mg UFT (TAIHO Pharmaceutical Co., Ltd.) for about a month (dose equal to or less than one-fifth of the normal dose) from Oct. 25, 2018 to Apr. 18, 2019. FIG. 7 shows (A) PET images and (B) CT images of the lung taken before and after administration of the sodium salt of hydrogencarbonate ions as a metabolite of potassium citrate•sodium citrate hydrate for half a year. From these results, complete elimination of the hilar and mediastinal lymph node metastasis and the multiple bone metastasis was observed. This non-small cell lung adenocarcinoma patient did not receive any of common cancer chemotherapy, high-dose vitamin C instillation therapy and oral administration of metformin as a diabetes drug.

[Example 8] Enhancing Effect on Anticancer Drug in Ovarian Cancer Patient

A patient having stage IVB ovarian cancer (57-year-old woman) received standard chemotherapy for ovarian cancer (combined use of paclitaxel and carboplatin) three times from January 2017, and received daily administration of a sodium salt of hydrogencarbonate ions as a metabolite of potassium citrate•sodium citrate hydrate at a dose of 15 g/day. As a result, the ovarian cancer began to shrink, and the level of CA125 as a blood tumor marker decreased. The effect was retained for about a year, but the ovarian cancer began to gradually increase in size from July 2018 (FIG. 8 shows (A) a PET image and (B) a CT image taken in July 2018), and the value of CA125 also increased to 199. Thus, while administration of the metabolite of potassium citrate•sodium citrate hydrate was continued, biweekly administration of an endoxan 50 mg tablet/day (amount equal to several tenths of normal amount) was started at Aug. 30, 2018. As a result, the value of CA125 began to gradually decrease, and decreased to 53 in February 2019, half a year later, and the pH of the urine was 8.5 (FIG. 8(C)). This patient did not receive either high-dose vitamin C instillation therapy or oral administration of metformin as a diabetes drug.

[Example 9] Enhancement of Anticancer Drug Effect by Citrate Salt

A cancer-bearing mouse (model obtained by subcutaneously implanting a mouse with a PANC-1 human pancreas cancer cell line) was caused to receive daily oral administration of a vehicle (control) for 2 weeks, daily oral administration of a tegafur•gimeracil•oteracil potassium combination drug (TS-1 (TAIHO Pharmaceutical Co., Ltd.) (hereinafter, referred to as "S-1") (18 mg/kg/day) for 2 weeks, daily oral administration of a potassium citrate•sodium citrate hydrate combination powder (Uralyt-U combination powder (Nippon Chemiphar Co., Ltd.), hereinafter, referred to as "Uralyt") (500 mg/kg/day) for 2 weeks, or daily oral administration of S-1 (18 mg/kg/day) and Uralyt (500 mg/kg/day) for 2 weeks, and the tumor volume and the body weight of the mouse were measured over time.

FIGS. 9(A) and 9(B) show the measured tumor volume (inhibitory effect on tumor growth) and the body weight of the mouse, respectively.

It is apparent from FIG. 9 (A) that a more significant inhibitory effect on tumor growth was exhibited in the group given a combination of S-1 (18 mg/kg/day) and Uralyt (500 mg/kg/day) than in the group given S-1 alone (18 mg/kg/day) and the group given Uralyt alone (500 mg/kg/day). That is, in the cancer-bearing mouse (model obtained by subcutaneously implanting a mouse with a PANC-1 human pancreas cancer cell line), enhancement of the antitumor effect of S-1 (18 mg/kg/day) (anticancer drug) by Uralyt (500 mg/kg/day) (alkaline agent) was observed.

It is apparent from FIG. 9(B) that there was no marked change in body weight in any of the administration groups. These results show that in the cancer-bearing mouse (model obtained by subcutaneously implanting a mouse with a PANC-1 human pancreas cancer cell line), use of S-1 (18 mg/kg/day) (anticancer drug) in combination with Uralyt (500 mg/kg/day) significantly enhanced the antitumor effect, and Uralyt (500 mg/kg/day) did not add toxicity to S-1 (18 mg/kg/day) (anticancer drug).

S-1, which is a 5-FU-type oral anticancer drug applicable to treatment of pancreas cancer etc., and is commonly used mainly in Japan. In typical dosage regimens with S-1, repeated oral administration is apt to cause toxicity involving a decline in platelets or the like, which poses a problem in treatment with S-1. However, it has been found that when S-1 is administered in combination with the citrate salt according to the present invention under conditions allowing high safety to be secured with the dose of S-1 reduced by about half, growth of cancer can be suppressed without worrying about side effects from S-1.

[Example 10] Medical Supply for Measuring pH of Urine

A pH test strip (BTB manufactured by Toyo Roshi Kaisha, Ltd. (pH 6.2 to 7.8)) was disposed on a water-absorbing material portion of an adult paper diaper (Relief Pants Type manufactured by Kao Corporation) to prepare a paper diaper capable of measuring the pH value of urine. A person with acidic urine (70-year-old man) was made to wear the prepared paper diaper, and before and after administration of a potassium citrate•sodium citrate hydrate 500 mg tablet (manufactured by Nippon Chemiphar Co., Ltd.) (at 4 to 6 tablets), a change in color of the pH test strip on the water-absorbing material portion of the paper diaper after urination was observed. The water-absorbing material portion of the paper diaper before the administration exhibited a yellow color indicating that the urine was acidic (pH 6.2), and the water-absorbing material portion of the paper diaper after the administration (several hours later) exhibited a light blue color indicating that the urine was alkalized (7.4). Use of the paper diaper enabled confirming that administration of the potassium citrate•sodium citrate hydrate tablet had a neutralizing effect on the urine of a patient with acidic urine.

The paper diaper capable of measuring the pH value of urine can serve as a medical supply for determining or confirming an ameliorating action on acidic urine (e.g. ameliorating action on acidic urine in high uric acid blood of elderly people), an ameliorating action on acidosis, and enhancing actions on the effects of cancer immunotherapeutic drugs such as an anti-PD-1 antibody and an anti-PDL-1 antibody, cancer molecular target drugs and cancer chemotherapeutic drugs, which are associated with administration of a pharmaceutical composition containing a citrate salt according to the present invention.

The invention claimed is:

1. A method for treating cancer, the method comprising administering (a) a combination of potassium citrate and sodium citrate hydrate and (b) a cancer immunotherapeutic drug to a cancer patient,
wherein vitamin C is not administered as an active ingredient for treating the cancer.

2. The method according to claim 1, wherein the combination of potassium citrate and sodium citrate hydrate is administered orally.

3. The method according to claim 1, wherein the cancer immunotherapeutic drug is an anti-PD-1 antibody.

4. The method of claim 1, wherein the combination of potassium citrate and sodium citrate hydrate is orally administered at a daily dose selected from the range of 1 to 20 g.

5. The method of claim 1, wherein the cancer is selected from melanoma, pancreatic cancer, breast cancer, colorectal cancer, non-small cell lung cancer, small cell lung cancer, gastric cancer and ovarian cancer.

6. The method of claim 1, wherein the cancer is selected from pancreatic cancer, breast cancer, colon cancer, non-small lung cancer, and ovarian cancer.

7. The method of claim 1, wherein the cancer is pancreatic cancer.

8. The method of claim 1, wherein the cancer is breast cancer.

9. The method of claim 1, wherein the cancer is non-small cell lung adenocarcinoma.

10. The method of claim 1, wherein the cancer is ovarian cancer.

11. The method of claim 1, wherein the cancer is colon cancer.

12. The method of claim 3, wherein the cancer is selected from pancreatic cancer, breast cancer, colon cancer, non-small lung cancer, and ovarian cancer.

13. The method of claim 3, wherein the cancer is pancreatic cancer.

14. The method of claim 3, wherein the cancer is breast cancer.

15. The method of claim 3, wherein the cancer is non-small cell lung adenocarcinoma.

16. The method of claim 3, wherein the cancer is ovarian cancer.

17. The method of claim 3, wherein the cancer is colon cancer.

18. The method of claim 3, wherein the combination of potassium citrate and sodium citrate hydrate is orally administered at a daily dose selected from the range of 1 to 20 g.

19. The method of claim 18, wherein the cancer is selected from pancreatic cancer, breast cancer, colon cancer, non-small lung cancer, and ovarian cancer.

20. The method of claim 4, wherein the cancer is selected from pancreatic cancer, breast cancer, colon cancer, non-small lung cancer, and ovarian cancer.

* * * * *